United States Patent
Nalladega et al.

(10) Patent No.: US 10,152,784 B2
(45) Date of Patent: Dec. 11, 2018

(54) SYSTEM AND METHOD FOR DETECTING DEFECTS IN A COMPONENT

(71) Applicant: General Electric Company, Schenectady, NY (US)

(72) Inventors: Venkata Vijayaraghava Nalladega, Niskayuna, NY (US); Thomas James Batzinger, Niskayuna, NY (US); Yuri Alexeyevich Plotnikov, Niskayuna, NY (US); Shyamsunder Tondanur Mandayam, Bangalore (IN); Bryon Edward Knight, Niskayuna, NY (US); Satheesh Jeyaraman, Bangalore (IN); Esha SenGupta, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 148 days.

(21) Appl. No.: 15/198,876

(22) Filed: Jun. 30, 2016

(65) Prior Publication Data
US 2018/0005368 A1    Jan. 4, 2018

(51) Int. Cl.
*G06T 7/00* (2017.01)
*G01N 25/72* (2006.01)
*G06T 5/50* (2006.01)

(52) U.S. Cl.
CPC ........... *G06T 7/0008* (2013.01); *G01N 25/72* (2013.01); *G06T 5/50* (2013.01);
(Continued)

(58) Field of Classification Search
None
See application file for complete search history.

(56) References Cited

U.S. PATENT DOCUMENTS

| | | |
|---|---|---|
| 3,020,745 A | 2/1962 | Sielicki et al. |
| 6,364,524 B1 | 4/2002 | Markham |

(Continued)

FOREIGN PATENT DOCUMENTS

| | | |
|---|---|---|
| EP | 1 267 161 A2 | 12/2002 |
| EP | 2 141 489 A1 | 1/2010 |

(Continued)

OTHER PUBLICATIONS

Abbasi et al., "NDE Inspections and Lifetime Assessment of Turbine Equipment", Power-Gen International 2008—Orlando, FL, pp. 1-11, Dec. 2-4, 2008.

(Continued)

*Primary Examiner* — Delomia L Gilliard
(74) *Attorney, Agent, or Firm* — GE Global Patent Operation; Nitin Joshi (57) ABSTRACT

A method for inspecting a component is presented. The method includes inducing, by an inductive coil, an electrical current flow into the component. Further, the method includes capturing, by an infrared (IR) camera, at least a first set of frames and a second set of frames corresponding to the component, wherein the first set of frames is captured at a first time interval and a second set of frames is captured at a second time interval. Also, the method includes constructing, by a processing unit, a thermal image based on at least the first set of frames and the second set of frames corresponding to the component. Furthermore, the method includes determining presence of a thermal signature in the thermal image, wherein the thermal signature is representative of a defect in the component.

24 Claims, 7 Drawing Sheets

(52) U.S. Cl.
CPC .............. *G06T 2207/10016* (2013.01); *G06T 2207/10048* (2013.01); *G06T 2207/20221* (2013.01)

(56) References Cited

U.S. PATENT DOCUMENTS

| | | | |
|---|---|---|---|
| 6,383,815 | B1 | 5/2002 | Potyrailo |
| 7,199,367 | B2 | 4/2007 | Favro et al. |
| 7,432,505 | B2 | 10/2008 | Brummel |
| 7,716,987 | B2 | 5/2010 | Sathish et al. |
| 8,287,183 | B2 | 10/2012 | Shepard et al. |
| 8,300,232 | B2 | 10/2012 | Sansom et al. |
| 8,440,974 | B2 | 5/2013 | Ruhge et al. |
| 8,527,215 | B2 | 9/2013 | Vrana et al. |
| 9,004,753 | B1 | 4/2015 | Maresca, Jr. et al. |
| 9,080,453 | B2 | 7/2015 | Shepard et al. |
| 9,194,831 | B2 * | 11/2015 | Traxler .................. G01N 25/72 |
| 2009/0046758 | A1 * | 2/2009 | Baumann ............... G01N 25/72 374/5 |
| 2010/0073665 | A1 | 3/2010 | Zhao et al. |
| 2010/0292938 | A1 * | 11/2010 | Vrana .................... G01N 25/72 702/35 |
| 2011/0249115 | A1 * | 10/2011 | Genest .................. G01N 25/72 348/125 |
| 2012/0002036 | A1 * | 1/2012 | Goldammer ........... G01N 25/72 348/86 |
| 2014/0063227 | A1 | 3/2014 | Baleine |
| 2015/0043769 | A1 | 2/2015 | Newman |
| 2015/0161778 | A1 * | 6/2015 | Henderkott .......... G06T 7/0008 348/129 |

FOREIGN PATENT DOCUMENTS

| | | | |
|---|---|---|---|
| JP | 2000206100 A | 7/2000 | |
| JP | 2001228105 A | 8/2001 | |
| JP | 2004012390 A | 1/2004 | |
| JP | 2006242887 A | 9/2006 | |
| JP | 2011214955 A | 10/2011 | |
| JP | 5026054 B2 | 9/2012 | |
| WO | WO 2008071204 A1 * | 6/2008 | ............. G01B 11/24 |

OTHER PUBLICATIONS

Zombo et al., "Advanced NDE Systems for Flexible Operation and Maintenance of Gas Turbine Components", Siemens Power Generation, Inc.—4400 N. Alafaya Trail, Orlando, FL 32826, pp. 13, Nov. 28-30, 2006.

Jussi Varis et al, "Photothermal Inspection of Impact Damages on Carbon-Glass Fibre Composites Using a Simple Hand Scanner Measurement Sysiem", Review of Progress in Quantitative Nondestructive Evaluation, vol. 12, Edited by D.O. Thompson and D.E. Chimenti, Plenum Press, New York, 1993, 5 Pages.

International Search Report and Written Opinion issued in connection with corresponding PCT Application No. PCT/US2017/039173 dated Oct. 2, 2017.

* cited by examiner

SYSTEM AND METHOD FOR DETECTING DEFECTS IN A COMPONENT

BACKGROUND

Embodiments of the present specification relate generally to inspection of a component and more particularly to a system and method for detecting defects in the component.

Typically, aircraft engines include one or more components that are made of nickel super alloys with thermal barrier coating (TBC) ranging from 6 mils to 15 mils. In one example, the components may be hot gas path components, such as high pressure turbine (HPT) blades or turbine buckets. During operation of the engines, these components may be subjected to stress or centrifugal force, which may cause cracks or other defects in the components. These cracks may occur below the TBC and hence, the cracks may not be visible to a user/inspector. Moreover, the cracks on these components may lead to a structural malfunction of the engine and may substantially damage the engine.

Conventionally, the components are either visually inspected or a fluorescent penetrant inspection (FPI) method is used to detect the cracks. As the cracks are underneath the TBC, it would be difficult for an operator to visually identify the cracks without removing the coating from the components. Also, the FPI method requires the TBC be removed from the components before inspection. Further, after inspection, the TBC is recoated prior to putting the components back in service. Removing the coating and recoating the components may substantially increase the cost associated with inspection of these components. In some cases, even though the components may not have developed cracks underneath the TBC at the time of inspection, however, since visual identification of presence or absence of such cracks is not feasible, the coating may be removed nevertheless for inspection. Hence, even if the cracks are not present underneath the TBC, the TBC needs to be removed and subsequently recoated, which in turn increases maintenance cost of the components. Moreover, both the visual inspection and the FPI method requires a trained operator to inspect the components and make a decision to scrap the components or send the components for repair.

BRIEF DESCRIPTION

In accordance with aspects of the present specification, a method for inspecting a component is presented. The method includes inducing, by an inductive coil, an electrical current flow into the component. Further, the method includes capturing, by an infrared (IR) camera, at least a first set of frames and a second set of frames corresponding to the component, wherein the first set of frames is captured at a first time interval and a second set of frames is captured at a second time interval. Also, the method includes constructing, by a processing unit, a thermal image based on at least the first set of frames and the second set of frames corresponding to the component. Furthermore, the method includes determining presence of a thermal signature in the thermal image, wherein the thermal signature is representative of a defect in the component.

In accordance with another embodiment of the present specification, a device for inspecting a component is presented. The device includes an inductive coil configured to induce an electrical current flow into the component. Further, the device includes an infrared (IR) camera configured to capture at least a first set of frames at a first time interval and a second set of frames at a second time interval, wherein the first and second set of frames correspond to at least a portion of the component. Also, the device includes a processing unit electrically coupled to the IR camera and configured to construct a thermal image based on at least the first set of frames and the second set of frames and determine presence of a thermal signature in the thermal image, wherein the thermal signature is representative of a defect in the component.

In accordance with yet another embodiment of the present specification a method for detecting multiple defects in a component is presented. The method includes translating, by a motion controller, an inductive coil within at least a portion of the component, wherein the portion of the component is disposed between a first end and a second end of the component. Further, the method includes inducing, by an inductive coil, an electrical current flow into the component, wherein the component includes at least a crack having a first orientation and a crack having a second orientation. Also, the method includes capturing, by an infrared (IR) camera, at least a first set of frames and a second set of frames corresponding to the component, wherein the first set of frames is captured at a first time interval and a second set of frames is captured at a second time interval. Furthermore, the method includes constructing, by a processing unit, a thermal image based on at least the first set of frames and the second set of frames corresponding to the component. In addition, the method includes determining presence of a first thermal signature associated with the crack having the first orientation and a second thermal signature associated with the crack having the second orientation in the thermal image of the component.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

As will be described in detail hereinafter, various embodiments of a system and method for inspecting a component for detecting presence or absence of defects are presented. In particular, the system and method presented herein detect one or more cracks in the component even if the cracks are underneath a thermal barrier coating (TBC) of the component. Also, the system and method presented herein may detect the cracks of any orientation on the component.

Figure 1:
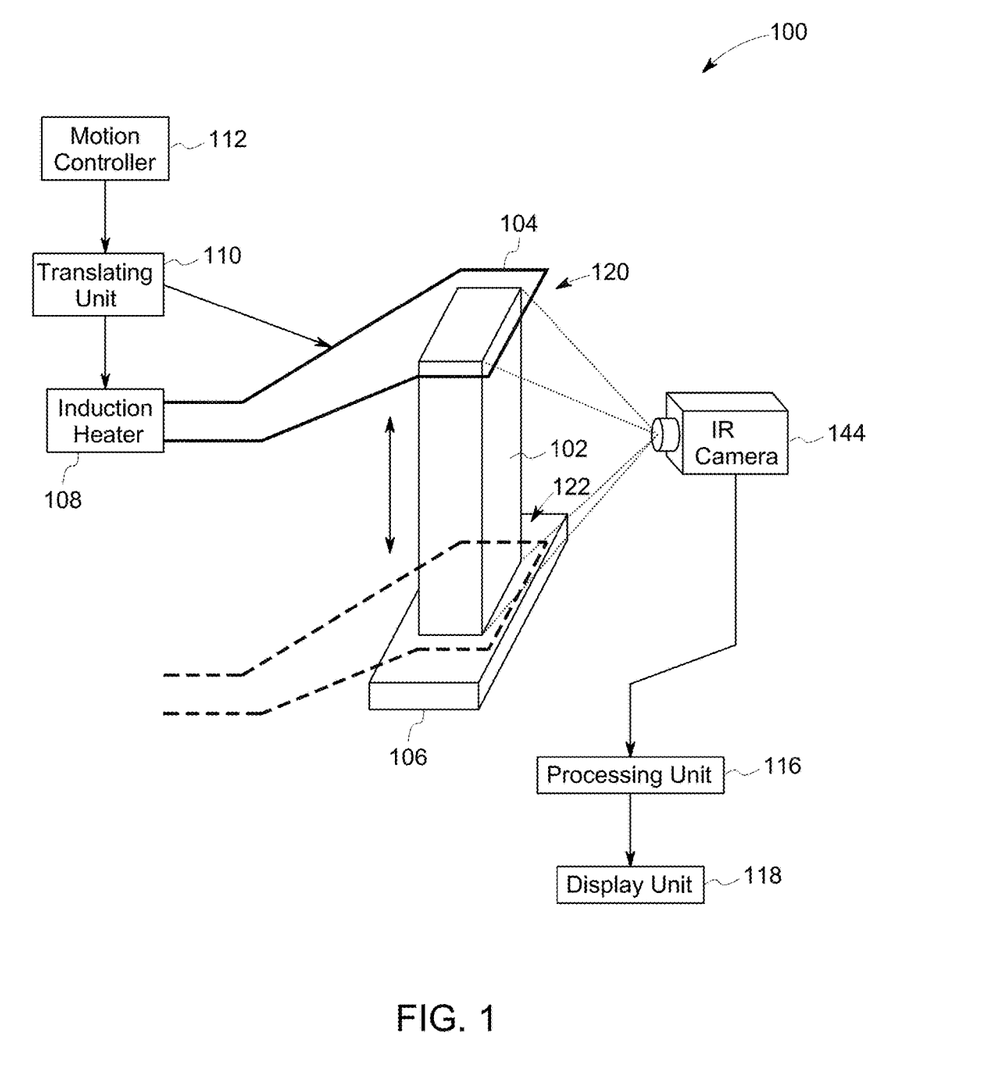
FIG. 1 illustrates a diagrammatical representation of a system for inspecting a component, in accordance with aspects of the present specification.

FIG. 1 illustrates a diagrammatical representation of a system 100 for inspecting one or more components 102, in accordance with aspects of the present specification. The components 102 may be components that are disposed in a path of hot gas in aircraft engines. In one example, the hot gas path components may include high pressure turbine (HPT) blades and turbine buckets. It may be noted that the components 102 may be any machinery components, and are not limited to the components used in aircraft engines. The description of components 102 in FIGS. 1-5 is with respect to HPT blades having a thermal barrier coating (TBC), however, other such components 102 are also envisioned within the purview of this application.

In a presently contemplated configuration, the system 100 includes an inductive coil 104, a base unit 106, an induction heater 108, a translating unit 110, a motion controller 112, an infrared (IR) camera 114, a processing unit 116, and a display unit 118. The component 102 that needs to be inspected is positioned or fastened to the base unit 106. In one example, the base unit 106 is configured to keep the component 102 stationary while inspecting the component 102.

Further, the inductive coil 104 is used to thermally scan the component 102 to detect defects, such as cracks in the component 102. In the illustrated example, the defects in the component 102 are referred to as cracks, however, other kinds of surface abnormalities may be detected by employing the systems and methods of the present application. It may be noted that a crack may be defined as an air gap on the surface of the component 102. Also, the crack may be of any orientation on the surface of the component 102. As depicted in FIG. 1, the inductive coil 104 is positioned around the component 102 and is configured to move or translate from a first end 120 to a second end 122 of the component 102, and vice-versa. In one example, the inductive coil 104 may be positioned proximate to the component 102. It may be noted that the inductive coil 104 may be of any shape so that the shape of the inductive coil 104 corresponds to a shape of at least a portion of the component 102. In particular, the shape of the inductive coil is such that the inductive coil is allowed to translate between the first end 120 to the second end 122 of the components 102.

Figure 2:
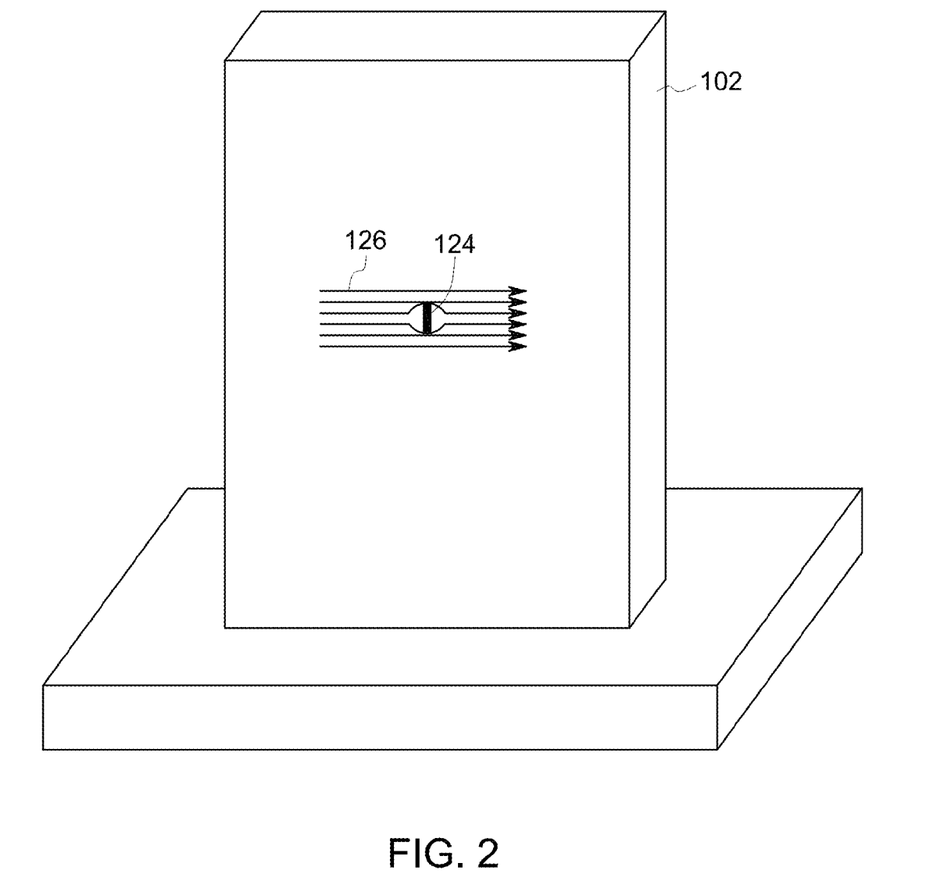
FIG. 2 is a diagrammatical representation of electrical current flow induced across a vertical crack in the component, in accordance with aspects of the present specification.

Further, the induction heater 108 is electrically coupled to the inductive coil 104 to energize or excite the inductive coil 104. In one example, the induction heater 108 may supply a power of up to 4 kW having a frequency in a range from about 100 kHz to about 400 kHz to energize the inductive coil 104. Further, the energized inductive coil 104 may induce an electrical current flow into the component 102. In one example, the electrical current may be in a range from about 100 A to about 200 A. This induced electrical current flow in the component may cause heat distribution across the component 102. However, if the component 102 includes one or more cracks, the heat distribution may be altered in the component 102. Particularly, as depicted in FIG. 2, the component 102 includes a crack having a first orientation, also referred to as a "vertical crack" 124. It may be noted that the terms "crack having a first orientation" and "vertical crack" may be used interchangeably throughout the application. It may be noted that the vertical crack 124 may refer to a crack that is substantially perpendicular to a direction of electrical current flow 126 into the component 102. In operation, the electrical current flow 126 induced in the component 102 is obstructed by this vertical crack 124 causing direct heating of the component 102 resulting in a first heating pattern at a location of the vertical crack 124. Further, it may be noted that the terms "first heating pattern" and "first thermal signature" may be used interchangeably in the below description.

Figure 3:
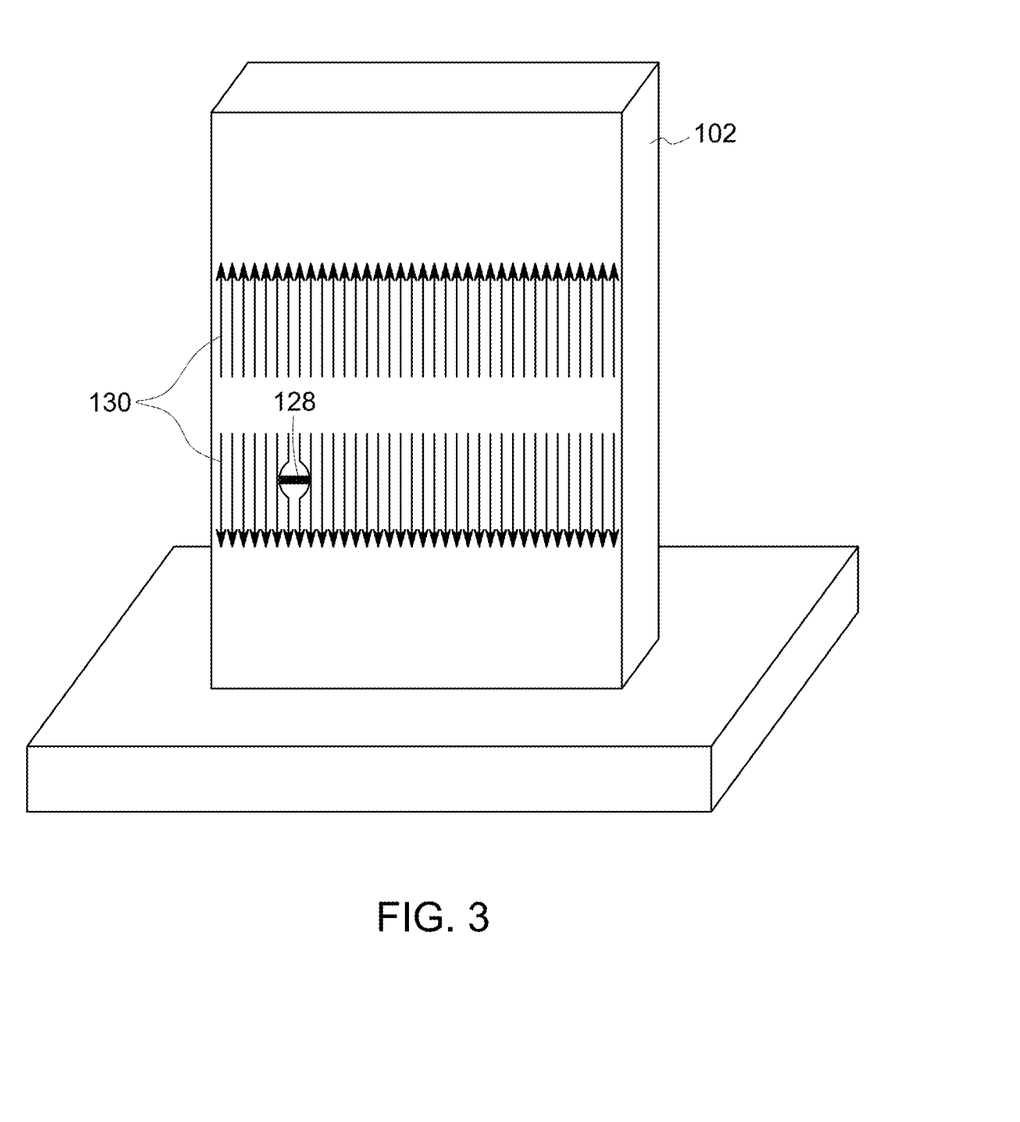
FIG. 3 is a diagrammatical representation of electrical current flow induced into the component that produces a lateral heat flow across a horizontal crack in the component, in accordance with aspects of the present specification.

In a similar manner, as depicted in FIG. 3, the component 102 includes a horizontal crack 128. It may be noted that the horizontal crack 128 may refer to a crack that is substantially parallel to a direction of electrical current flow 126 induced into the component. Further, the terms "horizontal crack" and "crack having a second orientation" may be used interchangeably throughout the patent application. In operation, the electrical current flow 126 induced in the component 102 may generate heat 130 that flows laterally or parallel to the direction of the electrical current flow 126. Also, this lateral heat flow 130 may be obstructed by the horizontal cracks 128 resulting in heat build-up at the horizontal crack 128. Consequently, a second heating pattern may be formed at a location of the horizontal cracks 128. The second heating pattern may be different from the first heating pattern. Further, it may be noted that the terms "second heating pattern" and "second thermal signature" may be used interchangeably throughout this application. Though the presently contemplated example is described with respect to a vertical and a horizontal crack, it may be noted that cracks having other orientations are also envisioned. In certain embodiments, a crack of any given orientation may be detected as the crack in the components 102 obstructs the electrical current flow 126, the later heat flow 130, or both thereby altering the heat distribution or resulting in different heating patterns at the location of the crack in the component 102.

Moving back to FIG. 1, the induction heater 108 includes cooling tubes (not shown in FIG. 1) that circulates water received from a chiller to prevent overheating of the induction heater 108 and the inductive coil 104. These cooling tubes are useful in preventing overheating of the induction heater 108 when a large number of components are scanned in a relatively short period.

Furthermore, the translating unit 110 and the motion controller 112 may be operatively coupled to the induction heater 108 to drive the inductive coil 104 across the component 102. Particularly, the translating unit 110 may be controlled by the motion controller 112 to translate the inductive coil 104 at a constant speed or in block-wise motion from the first end 120 to the second end 122 of the component 102, and vice-versa.

As depicted in FIG. 1, the IR camera 114 may be positioned at a predetermined distance from the component 102 to capture thermographic data of the component 102. In one example, the thermographic data may include two or more sets of frames captured at different time intervals when the inductive coil 104 is translated to different locations on the component 102. The component 102 may be within a field of view of the IR camera 114. In one example, the IR camera 114 may capture the thermographic data at a speed of 60 to 200 frames per second. Also, the IR camera 114 may operate in either mid-wave or long-wave range of infrared spectrum. In one embodiment, the scanning speed and heating time of the inductive coil 104 are adjusted based on the IR camera frame rate, which is typically between 60 Hz and 200 Hz.

Further, the processing unit 116 is electrically coupled to the IR camera 114 to process the thermographic data of the component 102 to detect one or more cracks 124, 128 in the component 102. In one example, the processing unit 116 may process two or more sets of frames captured at different time intervals to construct a thermal image of the component 102. It may be noted that the terms "thermal image," "processed thermal image," "constructed thermal image," and "constructed processed thermal image" may be used interchangeably. Further, the processing unit 116 may identify one or more thermal signatures in the constructed thermal image that are representative of the cracks 124, 128 in the component 102. It may be noted that a thermal signature may include a heating pattern on the surface of the component 102. The aspect of capturing thermographic data and processing the thermographic data to identify one or more cracks 124, 128 will be explained in greater detail with reference to FIGS. 4-5. The processing unit 116 may display the constructed thermal image on the display unit 118 to enable the user/operator to view the thermal signatures representative of one or more cracks 124, 128 in the component 102.

Advantageously, the systems and methods of the present application are configured to detect one or more cracks of same or different orientations on a surface of a component even when the surface of the component is covered during detection or inspection. By way of example, the surface of the component may be covered with a coating, a layer or foreign particles (e.g., dust, grease, chemical species, and the like). Further, the cracks may be completely or partly disposed underneath the coating or the layer. In the illustrated example of FIGS. 1-2, the cracks 124, 128 may be automatically detected by the system 100 without removing the TBC or any other coating from the component 102. Also, the cracks 124, 128 may be detected even if the component 102 is covered with dirt or other non-electrical layers.

Figure 4:
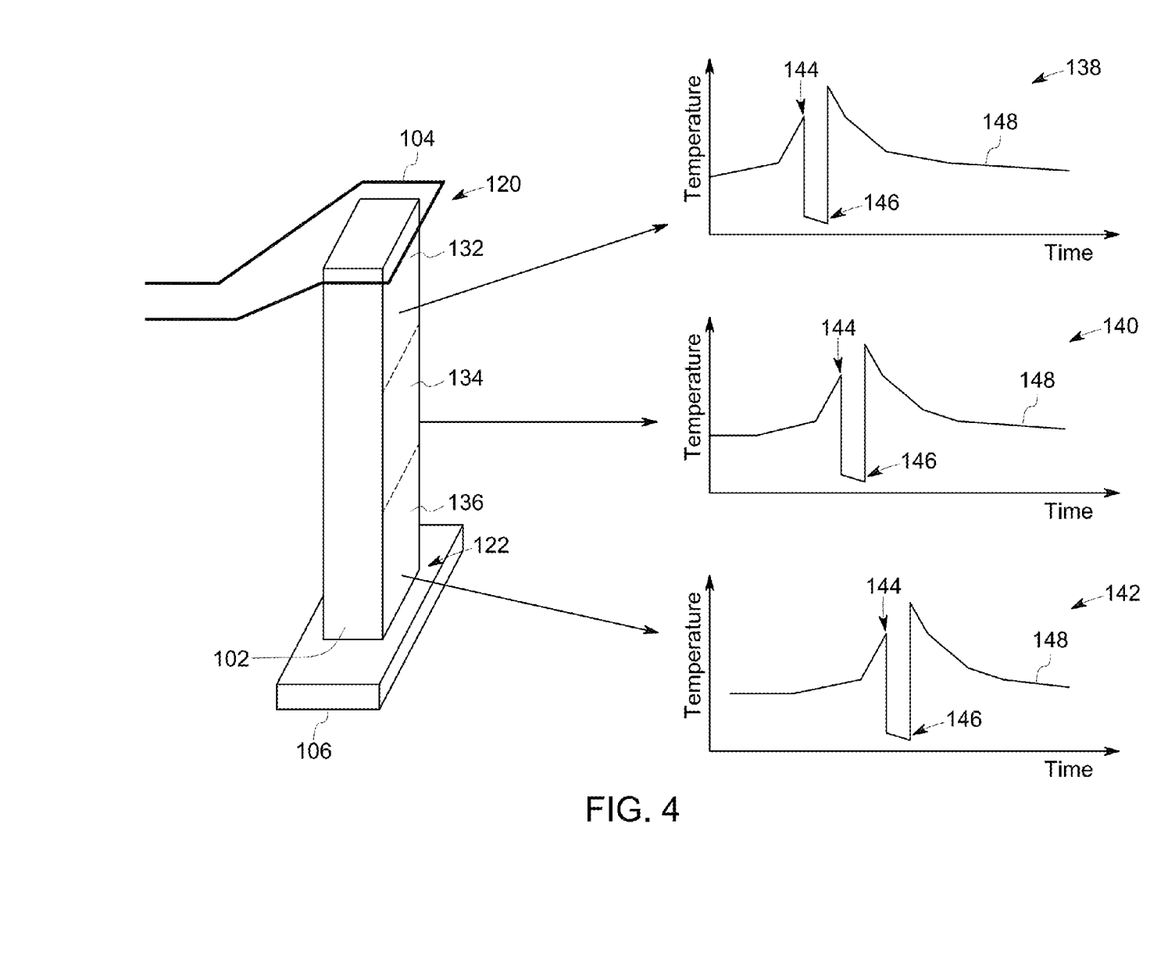
FIG. 4 is a diagrammatical representation of scanning the component to capture thermographic data of the component, in accordance with aspects of the present specification.

Referring to FIG. 4, a diagrammatical representation of scanning the component 102 to capture the thermographic data of the component 102, in accordance with aspects of the present specification is depicted. The component 102 is virtually segmented into a first area 132, a second area 134, and a third area 136. It may be noted that the component 102 may be segmented into any number, and is not limited to the segments or areas show in FIG. 4.

In a presently contemplated configuration, the inductive coil 104 is positioned around the component 102 at a first end 120. Further, the translating unit 110 along with the motion controller 112 may translate the inductive coil 104 from the first end 120 of the component 102 to the second end 122 of the component 102. Also, while translating the inductive coil 104, the induction heater 108 may energize or excite the inductive coil 104 to induce the electrical current flow 126 in the component 102. This induced electrical current flow 126 may generate and distribute heat across the component 102. This heat distribution in the component 102 is represented by temperature profiles. Particularly, thermographic data captured by the IR camera 114 when the inductive coil 104 is in the first area 132, is represented by a first temperature profile 138. Similarly, thermographic data captured by the IR camera 114 when the inductive coil 104 is in the second area 134, is represented by the second temperature profile 140. Also, thermographic data captured by the IR camera 114 when the inductive coil 104 is in the third area 136, is represented by the third temperature profile 142.

In each of the temperature profiles 138, 140, 142, greater values of temperatures represent instances during inspection of the component 102 when the inductive coil 104 is moved towards the cracks 124, 128. This increase in the temperature or thermal contrast is due to the cracks or air gaps 124, 128 present in the component 102 that obstruct the electrical current flow 126 and/or the lateral heat flow 130 in the component 102. This increase in temperature is represented by a reference numeral 144 in the temperature profiles 138, 140, 142. Further, when the inductive coil 104 translates below the IR camera 114, a portion of the component 102 is blocked from the IR camera 114. As a result, the thermographic data of the IR camera drops over this portion of the component 102. Also, in this portion of the component 102, the temperature may appear to drop, this drop in temperature is indicated by reference numeral 146 in the temperature profiles 138, 140, 142. Further, after the inductive coil 104 has passed over the blocked portion of the component 102, the temperature of the component 102 may start to gradually drop due to decrease in the electrical current flow and thermal exchange between the inductive coil 104 and the component 102. The temperature of the component 102 may continue to gradually drop until the component 102 reaches thermal equilibrium. This gradual drop in temperature is represented by reference numeral 148 in the temperature profiles 138, 140, 142.

Figure 5:
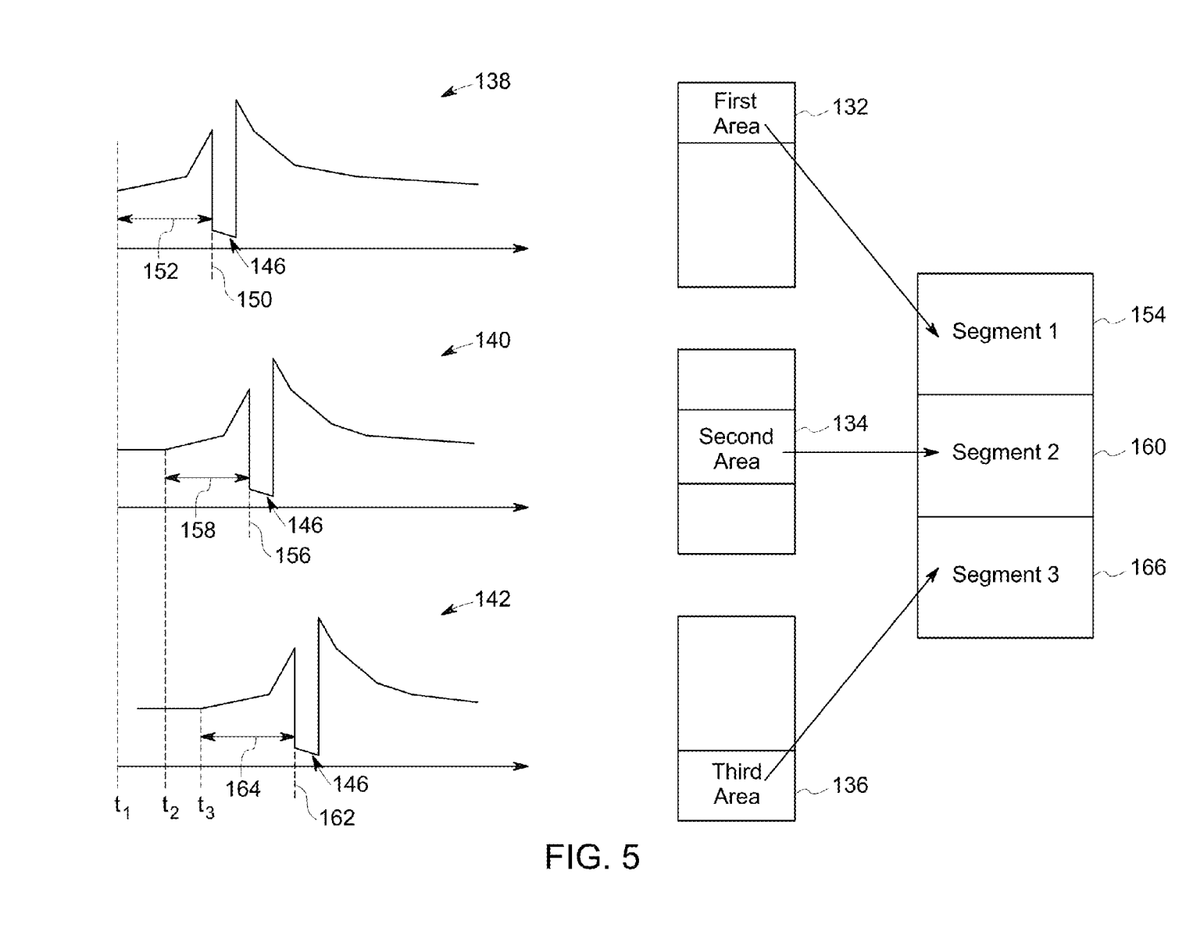
FIG. 5 is a diagrammatical representation of processing the thermographic data to construct a thermal image, in accordance with aspects of the present specification.

Referring to FIG. 5, a diagrammatical representation of processing the thermographic data to construct a thermal image, in accordance with aspects of the present specification, is depicted. The thermographic data may include one or more sets of frames captured by the IR camera 114. Particularly, in the first area 132, the thermographic data captured by the IR camera 114 may include a first set of frames. In the second area 134, the thermographic data captured by the IR camera 114 may include a second set of frames. Similarly, in the third area 136, the thermographic data captured by the IR camera 114 may include a third set of frames.

Further, the processing unit 116 may determine a first reference point 150 in the first temperature profile 138 that is immediately before the temperature drop 146. Also, the processing unit 116 may select a first sub-set of frames from the first set of frames that are within a first process period 152 before the first reference point 150 in the first temperature profile 138. This first sub-set of frames may include thermal signatures or heating patterns of the cracks or portions of cracks that are present in the first area 132. Also, the first sub-set of frames may correspond to a first image segment 154 of the component 102.

In a similar manner, the processing unit 116 may determine a second reference point 156 in the second temperature profile 140 that is immediately before the temperature drop 146. Also, the processing unit 116 may select a second sub-set of frames from the second set of frames that are within a second process period 158 before the second reference point 156 in the second temperature profile 140. This second sub-set of frames may include thermal signatures or heating patterns of the cracks in the second area 134. Also, the second sub-set of frames may correspond to a second image segment 160 of the component 102. In one embodiment, a portion of the second process period 158 may be overlapping on the first process period 152.

Furthermore, the processing unit 116 may determine a third reference point 162 in the third temperature profile 142 that is immediately before the temperature drop 146. Also, the processing unit 116 may select a third sub-set of frames from the third set of frames that are within a third process period 164 before the third reference point 162 in the third temperature profile 142. This third sub-set of frames may include thermal signatures or heating patterns of the cracks in the third area 136. Also, the third sub-set of frames may correspond to a third image segment 166 of the component.

In one embodiment, a portion of the third process period 164 may be overlapping on the second process period 158.

In the exemplary embodiment, the processing unit 116 may construct a thermal image by combining the first, second, and third sub-set of frames. In one example, the processing unit 116 may concatenate the first, second, and third image segments 154, 160 and 166 that are obtained from the corresponding sub-set of frames to construct the processed thermal image of the component 102.

In certain embodiments, the thermal image may be analyzed, for example, by the processing unit 116, to determine presence of one or more thermal signatures in the thermal image. These thermal signatures may be representative of cracks in the component 102. By way of example, if the component 102 includes the vertical crack 124, the thermal image may have a thermal signature corresponding to this vertical crack 124. This thermal signature corresponding to the vertical crack 124 may be referred to as a first thermal signature. Similarly, if the component 102 includes the horizontal crack 128, the thermal image may have a thermal signature corresponding to this horizontal crack 128. This thermal signature corresponding to the horizontal crack 128 may be referred to as a second thermal signature.

The processing unit 116 may process the thermal image to identify the first thermal signature and/or the second thermal signature in the thermal image of the component 102. In one embodiment, the first thermal signature and/or the second thermal signature may be determined in real time. Also, the thermal image indicating the first thermal signature and/or the second thermal signature may be displayed on the display unit 118.

Thus, by employing the system of the present application, such as the exemplary system 100, cracks, such as the cracks 124, 128, of any orientation may be detected in the component 102. Also, the exemplary system 100 may detect the cracks 124, 128 in a single scan of the component 102. Moreover, the exemplary system 100 is capable of detecting the cracks 124, 128 even if the component 102 is covered by thermal coating, dirt, and/or non-electrical layers.

Figure 6:
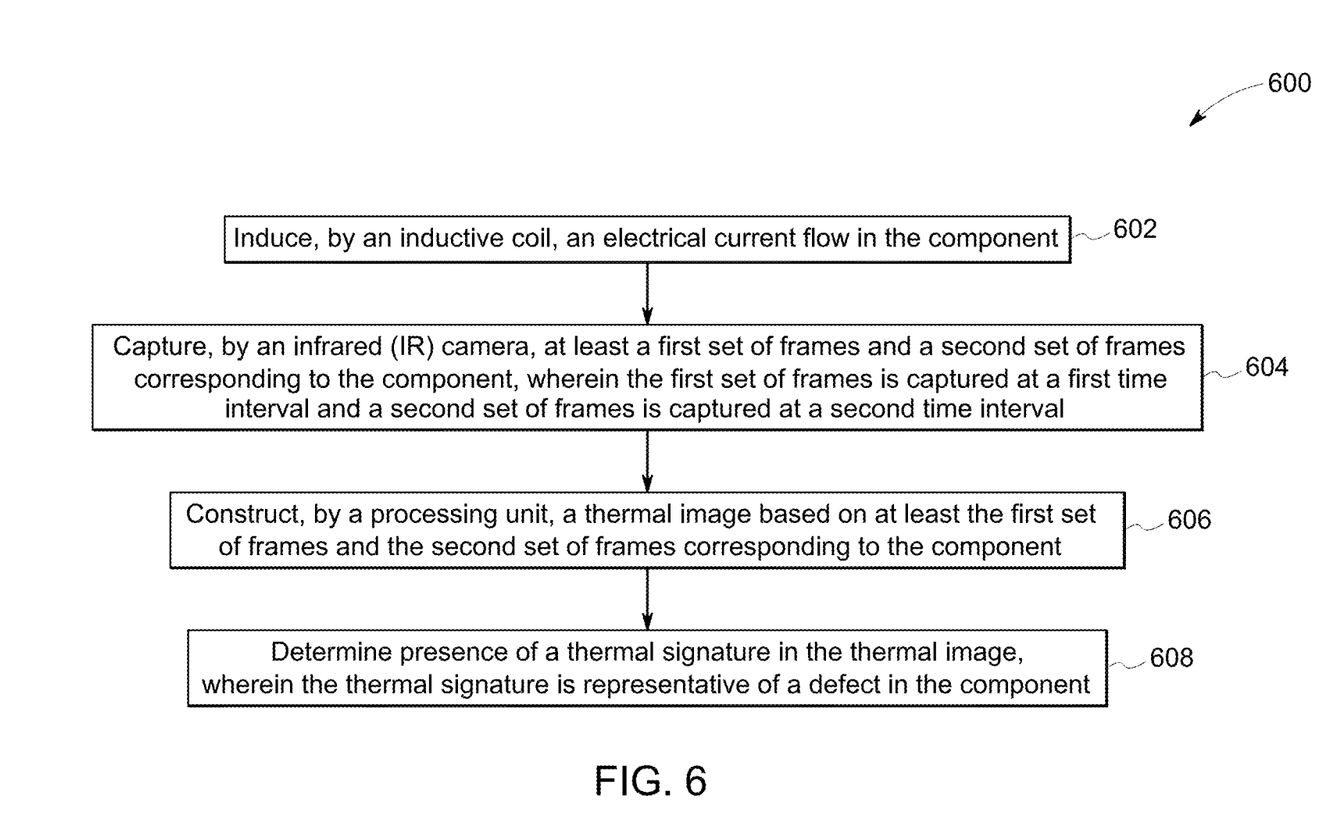
FIG. 6 is a flow chart illustrating a method for detecting defects in a component, in accordance with aspects of the present specification.

Referring to FIG. 6, a flow chart illustrating a method 600 for detecting defects in a component, in accordance with aspects of the present specification, is depicted. The method 600 is described with reference to the components of FIGS. 1-5. The method 600 begins at block 602, where an electrical current flow 126 is induced in the component 102. To that end, an inductive coil 104 is positioned proximate to the component 102. Further, the translating unit 110 in conjunction with the motion controller 112 translate the inductive coil 104 from the first end 120 of the component 102 to the second end 122 of the component 102. Also, while translating the inductive coil 104, the induction heater 108 may energize or excite the inductive coil 104 to induce the electrical current flow 126 in the component 102. This induced electrical current flow 126 may generate heat across the component 102, the generated heat may be distributed across a surface of the component 102.

Subsequently, at block 604, at least a first set of frames and a second set of frames corresponding to the component 102 may be captured at different time intervals. Particularly, when the inductive coil 104 is translated along a first area 132, the IR camera 114 may capture the first set of frames corresponding to the first area 132 of the component 102 at a first time interval. Further, when the inductive coil 104 is translated into a second area 134, the IR camera 114 may capture the second set of frames corresponding to the second area 134 of the component 102 at a second time interval.

Furthermore, at block 606, a thermal image is constructed based on at least the first set of frames and the second set of frames corresponding to the first and second areas 132 and 134 of the component 102. In one example, the processing unit 116 may select a first sub-set of frames from the first set of frames. The first sub-set of frames may be selected based on the first temperature profile 138 of the component 102. Further, the first sub-set of frames may correspond to a first image segment 154 of the component. Additionally, the processing unit 116 may select a second sub-set of frames from the second set of frames. The second sub-set of frames may be selected based on the second temperature profile 140 of the component 102. The second sub-set of frames may correspond to a second image segment 160 of the component 102. Thereafter, the processing unit 116 may combine the first sub-set of frames and the second sub-set of frames to construct at least in part a processed thermal image of the component 102.

Additionally, at block 608, the processing unit 116 may determine presence of a thermal signature in the constructed processed thermal image. The thermal signature is representative of a defect in the component 102. In one example, the processing unit 116 may determine the presence of a first thermal signature and/or a second thermal signature in the constructed processed thermal image. The first thermal signature may be indicative of a crack having a first orientation 124 in the component 102. The crack having the first orientation 124 is substantially perpendicular to a direction of the induced electrical current flow 126 in the component. Similarly, the second thermal signature is indicative of a crack having a second orientation 128 in the component 102. The crack having the second orientation 128 is substantially parallel to a direction of the induced electrical current flow 126 in the component 102.

Thus, by employing the exemplary method, cracks 124, 128 of any orientation may be detected in the component. Also, the method may detect the cracks even if the cracks are underneath TBC or any other non-electrical layers on the component 102.

Figure 7:
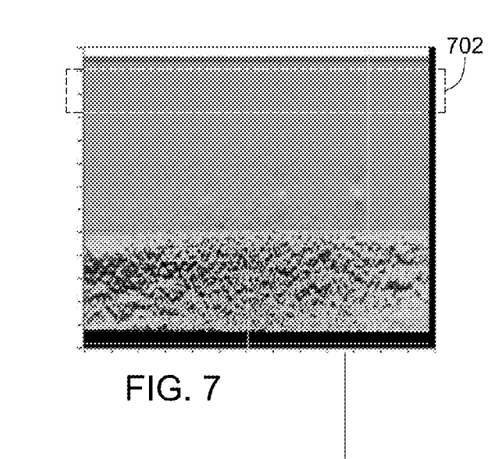
FIGS. 7-10 depict thermal images of the component, in accordance with aspects of the present specification.
Figure 8:
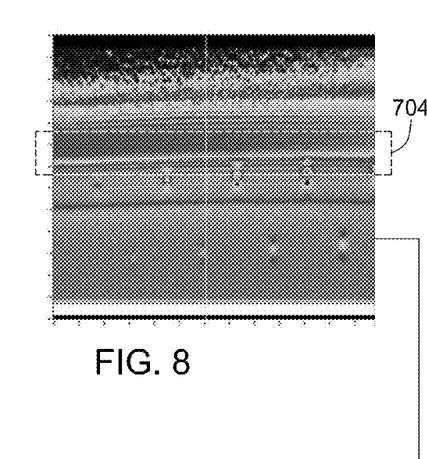
Figure 9:
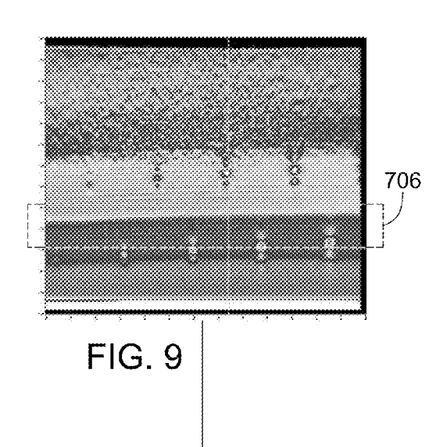

FIGS. 7-10 depict thermal images of the component 102, in accordance with aspects of the present specification. In FIG. 7, reference numeral 702 is representative of a first image segment 154 of FIG. 5. In this embodiment, the first image segment 702 is obtained by processing 200 sub-set of frames of thermographic data captured by the IR camera 114 over the first time interval 152 of 0.8 seconds. Similarly, in FIG. 8, reference numeral 704 is representative of a second image segment 160 of FIG. 5. In this embodiment, the second image segment 704 is obtained by processing 600 sub-set of frames of thermographic data captured by the IR camera 114 over the second time interval 158 of 2.4 seconds. Further, in FIG. 9, reference numeral 706 is representative of a third image segment 166 of FIG. 5. In this embodiment, the third image segment 706 is obtained by processing 800 sub-set of frames of thermographic data captured by the IR camera 114 over the third time interval 164 of 3.2 seconds.

Figure 10:
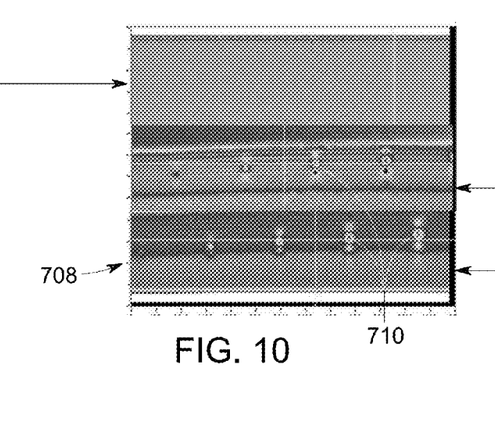

Further, in FIG. 10, the first image segment 702, the second image segment 704, and the third image segment 706 may be concatenated to obtain a constructed processed thermal image 708 that depicts one or more thermal signatures 710 representative of one or more cracks. Particularly, the constructed thermal image 708 may include a first thermal signature 710 or a heating pattern that is indicative of a vertical crack 124 or a crack of first orientation in the component 102. For ease of understanding, the constructed processed thermal image 708 having the first thermal signature 710 is depicted in FIG. 7. However, the constructed processed thermal image 708 may also include a second thermal signature that is indicative of a horizontal crack 128 or a crack of a different orientation than the first orientation in the component 102.

The various embodiments of the exemplary system and method aid in automatically detecting one or more cracks in the component. Also, the cracks in the component are detected without removing the coating, direct, and/or other non-electrical layers on the component. This in turn reduces the inspection cost and maintenance cost of the component.

While only certain features of the present disclosure have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A method for inspecting a component, the method comprising:
   inducing, by an inductive coil, an electrical current flow into the component;
   capturing, by an infrared (IR) camera, thermographic data of the component, wherein the thermographic data comprises at least a first set of frames corresponding to a first area of the component at a first time interval and a second set of frames corresponding to a second area of the component at a second time interval different from the first time interval;
   determining, by a processing unit, a first reference point in the thermographic data of the first set of frames based on a drop in temperature at a portion of the component, wherein the first reference point indicates that the portion of the component is blocked from the IR camera;
   determining, by the processing unit, a second reference point in the thermographic data of the second set of frames based on a drop in temperature at an another portion of the component, wherein the second reference point indicates that the another portion of the component is blocked from the IR camera;
   selecting, by the processing unit, a first sub-set of frames from the first set of frames, wherein the first sub-set of frames is selected within a first process period before the first reference point;
   selecting, by the processing unit, a second sub-set of frames from the second set of frames, wherein the second sub-set of frames is selected within a second process period before the second reference point;
   constructing, by the processing unit, a thermal image based on at least the first sub-set of frames and the second sub-set of frames corresponding to the component; and
   determining presence of a thermal signature in the thermal image, wherein the thermal signature is representative of a defect in the component.

2. The method of claim 1, wherein constructing the thermal image comprises:
   combining the first sub-set of frames and the second sub-set of frames to construct at least in part the thermal image of the component.

3. The method of claim 2, wherein the thermal signature comprises one of a first thermal signature and a second thermal signature in the thermal image of the component.

4. The method of claim 3, wherein the first thermal signature is indicative of a crack having a first orientation in the component, wherein the crack having the first orientation is perpendicular to a direction of the induced electrical current flow in the component.

5. The method of claim 4, wherein the second thermal signature is indicative of a crack having a second orientation in the component, wherein the crack having the second orientation is parallel to the direction of the induced electrical current flow in the component.

6. The method of claim 1, further comprising:
   positioning, by a motion controller, the inductive coil around the component; and
   translating, by the motion controller, the inductive coil within at least a portion of the component, where the portion of the component is disposed between a first end and a second end of the component.

7. The method of claim 6, further comprising disposing the IR camera at a predetermined distance from the component prior to translating the inductive coil.

8. A device for inspecting a component, the device comprising:
   an inductive coil configured to induce an electrical current flow into the component;
   an infrared (IR) camera configured to capture thermographic data of the component, wherein the thermographic data comprises at least a first set of frames corresponding to a first area of the component at a first time interval and a second set of frames corresponding to a second area of the component at a second time interval;
   a processing unit electrically coupled to the IR camera and configured to:
      determine a first reference point in the thermographic data of the first set of frames based on a drop in temperature at a portion of the component, wherein the first reference point indicates that the portion of the component is blocked from the IR camera;
      determine a second reference point in the thermographic data of the second set of frames based on a drop in temperature at an another portion of the component, wherein the second reference point indicates that the another portion of the component is blocked from the IR camera;
      selecting a first sub-set of frames from the first set of frames, wherein the first sub-set of frames is selected within a first process period before the first reference point;
      selecting a second sub-set of frames from the second set of frames, wherein the second sub-set of frames is selected within a second process period before the second reference point;
      construct a thermal image based on at least the first sub-set of frames and the second sub-set of frames; and
      determine presence of a thermal signature in the thermal image, wherein the thermal signature is representative of a defect in the component.

9. The device of claim 8, further comprising a motion controller operatively coupled to the inductive coil and configured to translate the inductive coil within at least a portion of the component disposed between a first end of the component and a second end of the component.

10. The device of claim 9, wherein the inductive coil is inductively positioned around the component prior to translating the inductive coil.

11. The device of claim 8, wherein the processing unit is configured to:

combine the first sub-set of frames and the second sub-set of frames to construct at least in part the thermal image of the component.

12. The device of claim 11, wherein the thermal signature comprises one of a first thermal signature and a second thermal signature in the thermal image of the component.

13. The device of claim 12, wherein the processing unit is configured to identify the first thermal signature indicative of a crack having a first orientation in the component, wherein the crack having the first orientation is perpendicular to a direction of the induced electrical current flow in the component.

14. The device of claim 13, wherein the processing unit is configured to identify the first thermal signature when the component is heated directly by the electrical current flow across the crack having the first orientation in the component.

15. The device of claim 13, wherein the processing unit is configured to identify the second thermal signature indicative of a crack having a second orientation in the component, wherein the crack having the second orientation is parallel to the direction of the electrical current flow in the component.

16. The device of claim 15, wherein the processing unit is configured to identify the second thermal signature when the component is heated by a lateral heat flow across the crack having the second orientation in the component.

17. The device of claim 8, wherein a shape of the inductive coil corresponds to a shape of at least a portion of the component.

18. The device of claim 8, further comprising a display unit electrically coupled to the processing unit and configured to display the thermal image.

19. The device of claim 8, wherein the processing unit is configured to determine the thermal signature in the thermal image in real time.

20. The device of claim 8, wherein the component is coated with at least one non-electrical layer or covered with dirt, and wherein the processing unit is configured to determine the defect in the component that is coated with the at least one non-electrical layer or covered with the dirt.

21. A method for detecting multiple defects in a component, the method comprising:
    translating, by a motion controller, an inductive coil within at least a portion of the component, wherein the portion of the component is disposed between a first end and a second end of the component;
    inducing, by the inductive coil, an electrical current flow into the component, wherein the component comprises at least a crack having a first orientation and a crack having a second orientation;
    capturing, by an infrared (IR) camera, thermographic data of the component, wherein the thermographic data comprises at least a first set of frames corresponding to a first area of the component at a first time interval and a second set of frames corresponding to a second area of the component at a second time interval different from the first time interval;
    determining, by a processing unit, a first reference point in the thermographic data of the first set of frames based on a drop in temperature at a portion of the component, wherein the first reference point indicates that the portion of the component is blocked from the IR camera;
    determining, by the processing unit, a second reference point in the thermographic data of the second set of frames based on a drop in temperature at an another portion of the component, wherein the second reference point indicates that the another portion of the component is blocked from the IR camera;
    selecting, by the processing unit, a first sub-set of frames from the first set of frames, wherein the first sub-set of frames is selected within a first process period before the first reference point;
    selecting, by the processing unit, a second sub-set of frames from the second set of frames, wherein the second sub-set of frames is selected within a second process period before the second reference point;
    constructing, by the processing unit, a thermal image based on at least the first sub-set of frames and the second sub-set of frames corresponding to the component; and
    determining presence of a first thermal signature associated with the crack having the first orientation and a second thermal signature associated with the crack having the second orientation in the thermal image of the component.

22. The method of claim 21, wherein capturing at least the first set of frames and the second set of frames comprises:
    positioning the IR camera at a predetermined distance from the component; and
    capturing at least the first set of frames and the second set of frames when the inductive coil translates between the first end and the second end of the component.

23. The method of claim 21, wherein constructing the thermal image comprises:
    combining the first sub-set of frames and the second sub-set of frames to construct at least in part the thermal image of the component.

24. The method of claim 21, wherein the first thermal signature and the second thermal signature are determined in real time.

* * * * *